United States Patent
Goertler et al.

(10) Patent No.: US 9,844,457 B1
(45) Date of Patent: Dec. 19, 2017

(54) MALE ERECTION ENHANCEMENT LOOP

(71) Applicants: Angela Arlene Goertler, West Richland, WA (US); James Lee Goertler, West Richland, WA (US)

(72) Inventors: Angela Arlene Goertler, West Richland, WA (US); James Lee Goertler, West Richland, WA (US)

( * ) Notice: Subject to any disclaimer, the term of this patent is extended or adjusted under 35 U.S.C. 154(b) by 454 days.

(21) Appl. No.: 14/544,127

(22) Filed: Nov. 25, 2014

(51) Int. Cl.
*A61F 5/00* (2006.01)
*A61F 5/41* (2006.01)

(52) U.S. Cl.
CPC .......... *A61F 5/41* (2013.01); *A61F 2005/414* (2013.01)

(58) Field of Classification Search
CPC ............................. A61F 5/41; A61F 2005/414
USPC .......................................... 600/38–41, 9, 15
See application file for complete search history.

(56) References Cited

U.S. PATENT DOCUMENTS

| | | | | |
|---|---|---|---|---|
| 6,508,749 B1 * | 1/2003 | Broadwater | ....... | A63B 21/0552 482/121 |
| 7,645,228 B2 * | 1/2010 | Flores | ....... | A61F 5/41 600/38 |
| 8,033,984 B2 * | 10/2011 | Kozak | ....... | A61F 5/41 600/15 |
| 2008/0072622 A1 * | 3/2008 | Brack | ....... | A44C 5/0023 63/3 |

* cited by examiner

*Primary Examiner* — Samuel Gilbert
(74) *Attorney, Agent, or Firm* — Risto A. Rinne, Jr.

(57) ABSTRACT

An apparatus for decreasing the adverse effect of erectile dysfunction includes an elastic waist band. A plurality of magnets are disposed in a generally end to end orientation to provide a magnetic loop assembly. A cloth sleeve preferably surrounds the magnets. The waist band encircles a waist of the user. Opposite ends of the magnetic loop assembly are secured in a spaced-apart relationship to a front portion of the waist band and to form a loop that descends below the waist band. Opposite ends of an elastic thigh band are attached to a rear portion of the waist band. A center of the magnetic tube assembly is attached to a center of the thigh band. The male enhancement loop is worn for a period of time prior to intercourse to help to improve the quality (i.e., hardness) and duration of male erection during intercourse.

12 Claims, 2 Drawing Sheets

MALE ERECTION ENHANCEMENT LOOP

BACKGROUND OF THE INVENTION

1. Field of the Invention

The present invention, in general, relates to erectile dysfunction and, more particularly, to a device that is worn proximate the male genital organs to improve erection capability.

Erectile dysfunction is a well-known phenomenon that affects many men, especially as they age. We are fortunate today to have medicines available that can provide improved erection performance.

However, these medicines all also have side-effects. These vary from product to product and from user to user. Some of the more common side-effects include degradation of olfactory capability, a lowering of blood pressure, and headaches, among others. For some people, the side-effects are serious enough to preclude the use of these medicines.

Therefore, there is a need for a treatment that can obviate or lessen the severity of erectile dysfunction and which has fewer side-effects. Ideally, a treatment that had no adverse side-effects and which improved male erection performance is especially desirable.

Commonly available drug therapies for erectile dysfunction also dilate certain of the blood vessels. There is an increased risk of possible discharge of plaque from inside blood vessels (i.e., artery interior walls) during dilation, especially in the presence of coronary disease. As this can be potentially serious or even fatal, it is an undesirable side-effect.

Accordingly, there is a need to treat erectile dysfunction without increasing the risk of release of plaque, as with vasodilator types of drug therapies.

Erectile dysfunction is potentially harmful to intimate relationships, regardless of how understanding a partner may be. An inability to perform can adversely affect a man's sense of self-worth, or self-esteem. This can start a negative spiral of self-doubt. The next time the man tries to perform sexually a portion, perhaps a significant portion, of his awareness is then directed toward his own ability to perform rather than on enjoying the sex act of itself. This redirection of focus away from the pleasure of sex to one's own performance or lack of performance detracts from the joy, spontaneity and pleasure of intercourse and, even worse, it can easily create an ever-worsening pattern of increasing self-doubt with regard to performance and a resulting increase in dysfunction.

One goal, therefore, is to interrupt the potentially downward cycle of male sexual dysfunction. Medicine is one option to that end. And, up to now it has largely been the only practical option available.

A portion of the efficacy of erectile dysfunction therapies is that, by giving the man hope and reason to believe that he will perform better, he puts more attention on pleasing his partner and on the pleasure he derives from the sexual contact while putting less awareness on his own performance. This results in a decrease of awareness during intercourse that is focused on one's own moment-by-moment state of arousal (i.e., the quality of erection) and instead focused more on the pleasure (giving and receiving) of the moment.

This therapeutic benefit is significant. The increased focus on pleasure can only help to increase sexual arousal and physical stimulation which, in turn, may help to improve sexual response (i.e., the quality of erection). This then sets up a pattern of positive reinforcement feedback. The man feels better about his sexual performance and so he feels less need to worry about and monitor the state of his erection. He focuses even more on the sex act itself, which again may still further increase sexual arousal and stimulation and thereby further improve the quality of erection.

It is to be understood that this benefit is not universally applicable to all men. Some men suffer from severely compromised blood flow and other physical disorders that are beyond all psychological remedy. However, most men with less than severe erectile dysfunction stand to benefit from any therapy that helps them to believe that they will experience improved performance.

This is, of course, a well-known phenomenon that occurs with many medicines and therapies and is referred to as the placebo effect. What is significant about erectile dysfunction is that, to a man, his ability to perform sexually is intimately tied to his sense of self and self-worth and, consequently, to where he directs his attention during intercourse. Therefore, a little placebo effect can go a disproportionately long way toward improving sexual performance for many men.

Additionally, there are various treatments that science is still unclear as to the causal factor or mechanism of improvement. Sometimes, the fact that certain treatments work well is, for the time being, simply good-enough. Science often later determines the causal nature and the clinical mechanism of action. This is true for many prescribed medicines intended to treat a particular malady. Often, quite by accident, a clear and compelling therapeutic benefit in the treatment of an entirely different disorder occurs. In other words, the medicine may provide a surprise therapeutic benefit for a different disease or pathology than it was originally intended to help. The cause of this surprise benefit may remain a mystery for an indefinite period of time. Yet, the benefit is still there. This can be viewed as a beneficial type of side-effect of the medicine that can be used to treat other maladies, even while the mechanism of action remains unknown.

Similarly, many over-the-counter supplements provide clinically proven improvement with currently either no or only partial knowledge as to the pharmacological mechanism of action. Yet they, too, may be quite effective.

In general, anything that improves blood flow to the penis during sexual arousal is desirable in the treatment of erectile dysfunction. Therefore, regardless of the mechanism of action, whether completely understood or not, additional treatment options for erectile dysfunction are needed.

As mentioned above, certain medical conditions, such as coronary artery disease may preclude the use of currently-available erectile dysfunction medicines. Therefore, there is a need for an erectile dysfunction therapy that can be used in the presence of other medical conditions (i.e., which is not contraindicated).

Accordingly, there exists today a need for a male erection enhancement loop that helps to ameliorate the above-mentioned problems and difficulties as well as ameliorate those additional problems and difficulties as may be recited in the "OBJECTS AND SUMMARY OF THE INVENTION" or discussed elsewhere in the specification or which may otherwise exist or occur and that are not specifically mentioned herein.

As various embodiments of the instant invention help provide a more elegant solution to the various problems and difficulties as mentioned herein, or which may otherwise exist or occur and are not specifically mentioned herein, and by a showing that a similar benefit is not available by mere reliance upon the teachings of relevant prior art, the instant invention attests to its novelty. Therefore, by helping to provide a more elegant solution to various needs, some of which may be long-standing in nature, the instant invention further attests that the elements thereof, in combination as claimed, cannot be obvious in light of the teachings of the prior art to a person of ordinary skill and creativity.

Clearly, an apparatus that provides improvement to erectile dysfunction would be useful and desirable.

2. Description of Prior Art

Medicinal treatments of erectile dysfunction are, in general, known. While the objective of the above described solutions is similar to that of the current invention, these approaches to treating erectile dysfunction differ in material respects. These differences, which will be described in more detail hereinafter, are essential for the effective use of the invention and which admit of the advantages that are not available with the prior medicine-based solutions.

OBJECTS AND SUMMARY OF THE INVENTION

It is an object of the present invention to provide a male erection enhancement loop that improves male erectile (i.e., erection) performance.

It is also an important object of the invention to provide a male erection enhancement loop that can be worn by a man.

Another object of the invention is to provide a male erection enhancement loop that can be worn by a man and which is not visible or apparent to others who may observe the man.

Still another object of the invention is to provide a male erection enhancement loop that eliminates at least some of the side-effects of a medicine-based treatment for erectile dysfunction.

Still yet another object of the invention is to provide a male erection enhancement loop that is inexpensive to manufacture, and therefore is less expensive to offer for public purchase.

Still yet another important object of the invention is to provide a male erection enhancement loop that can be worn for extended periods of time and which can be removed prior to intercourse or worn during intercourse while providing a therapeutic benefit.

A first continuing object of the invention is to provide a male erection enhancement loop that improves blood flow to the penis.

A second continuing object of the invention is to provide a male erection enhancement loop that provides a positive expectation for a man regarding his sexual performance.

A third continuing object of the invention is to provide a male erection enhancement loop that is available in a variety of sizes.

A fourth continuing object of the invention is to provide a male erection enhancement loop that is thin and lightweight.

A fifth continuing object of the invention is to provide a male erection enhancement loop that includes a plurality of magnets a portion of which are disposed under a penis and testicles.

A sixth continuing object of the invention is to provide a male erection enhancement loop that includes a plurality of hollow magnets that are placed in an end to end fashion within a sleeve and are disposed under a penis and testicles.

A seventh continuing object of the invention is to provide a male erection enhancement loop that may help to improve blood flow to the penis during sexual intercourse.

Briefly, a male erection enhancement loop that is constructed in accordance with the principles of the present invention includes a plurality of small cylindrical magnets that each include an opening, there-through. The magnets are disposed over a thin monofilament line or other preferred type of cord so that they are adjacent with respect to each other, in a positive adjacent to a negative polarity. A cloth sleeve surrounds the magnets and forms a magnetic tube assembly. An elastic waist band encircles a waist of a user. Opposite ends of the cloth sleeve are secured in a spaced-apart relationship with respect to each other to a front portion of the waist band. The magnetic tube assembly forms a loop that is attached at opposite ends, thereof, to the waist band and thereby descends below the waist band. An elastic thigh band is attached on opposite ends, thereof, to a rear portion of the waist band. The thigh band forms a second loop that also descends below the waist band. A center of the magnetic tube assembly is attached to a center of the thigh band. The male enhancement loop is worn in a manner similar to wearing underpants. When properly worn, a portion of the magnetic tube assembly is disposed under the testicles and penis. The male erection enhancement loop must be worn for a period of time prior to intercourse, after which, the male erection enhancement loop helps to improve the quality of male erection for those men who have certain types of erectile dysfunction. Optimum benefit is typically realized after the male erection enhancement loop has been worn for approximately three days. It is not necessary that the male erection enhancement loop be worn during actual intercourse.

DETAILED DESCRIPTION OF THE INVENTION

Figure 1:
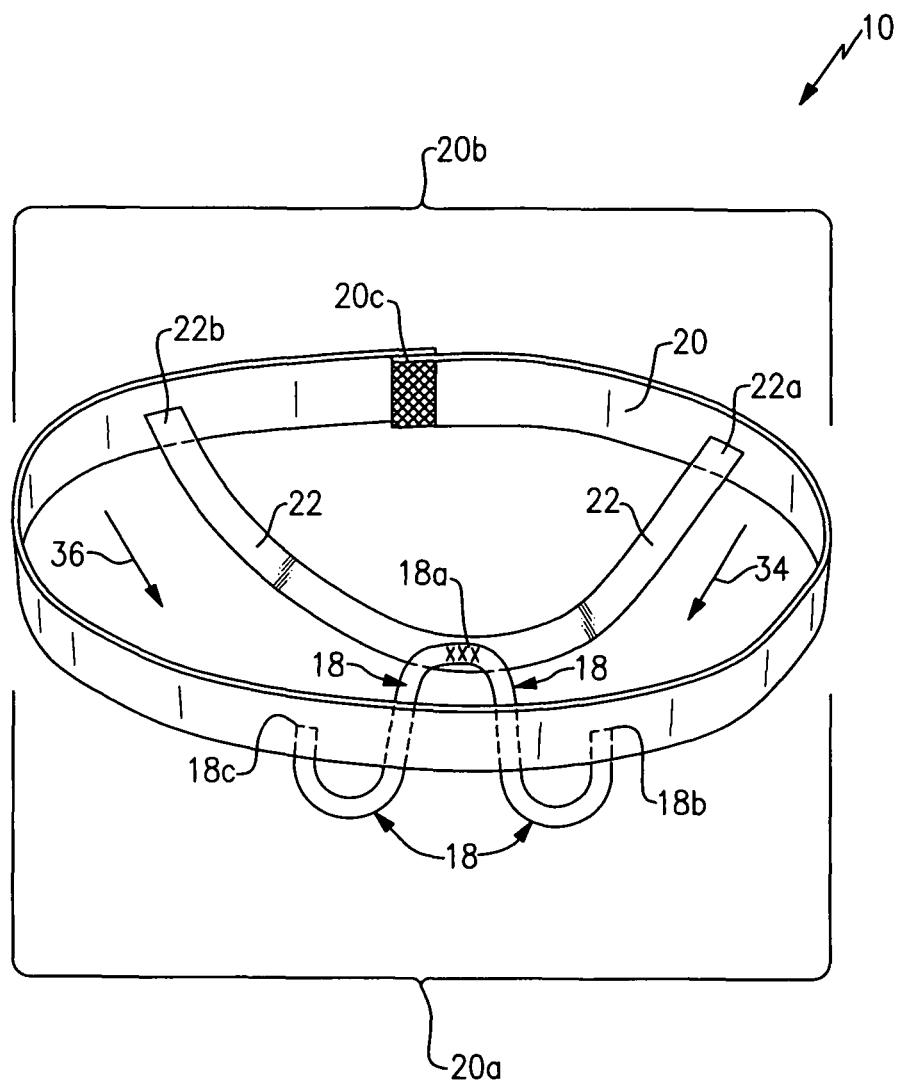
FIG. 1 is a view in perspective of a male erection enhancement loop.

Referring on occasion to all of the FIGURE drawings and now, in particular to FIG. 1, is shown a male erection enhancement loop, identified in general, by the reference numeral 10.

The reader will notice that reference is occasionally made throughout the DETAILED DESCRIPTION OF THE INVENTION suggesting that the reader refer to a particular drawing FIGURE. The suggestion is at times made when the introduction of a new element requires the reader to refer to a different drawing FIGURE than the one currently being viewed and also when the timely viewing of another drawing FIGURE is believed to significantly improve ease of reading or enhance understanding. To promote rapid understanding of the instant invention the reader is encouraged to periodically refer to and review each of the drawing FIGURES for possible cross-referencing of component parts and for other potentially useful information.

The male enhancement loop 10 includes a plurality of small cylindrical magnets 12. The magnets 12 each include an opening that extends fully through a center of the magnets 12 from one end to an opposite end. A preferred type of the magnets 12 is commonly referred to as hematite magnetic rice beads. A preferred size is commonly referred to as "size 5×7".

Figure 2:
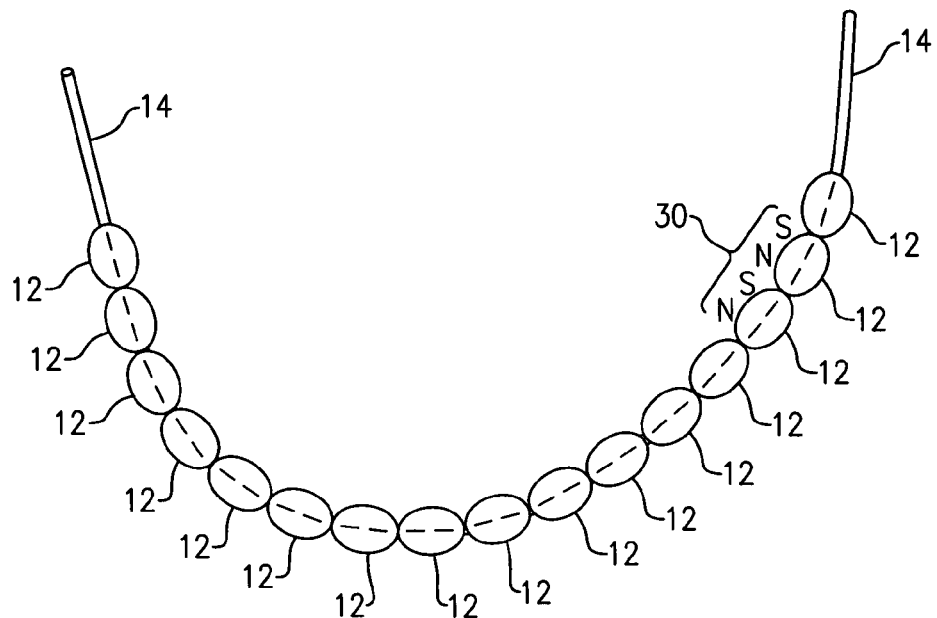
FIG. 2 is a plan view of a partially completed magnetic tube assembly that, at present, includes a plurality of magnets disposed over a monofilament line.

Referring now in particular to FIG. 2, a monofilament line 14 is inserted through the opening of each of magnets 12 with the ends of adjacent magnets 12 generally touching one-another. A gap may exist between certain of the magnets 12. This is described in greater detail, herein below. Also, the two top-most magnets 12 will each only be adjacent to a lower one of the remaining magnets 12.

Although use of the monofilament line 14 is preferred, any other preferred type of string, twine or cord may, instead, be used. It is important to note that the magnets 12 are placed over the monofilament line 14 in a positive or north pole adjacent to a negative or south pole magnetic polarity. For example, see bracket 30 which shows the south pole of a lower one of the magnets 12 disposed adjacent to the north pole of an upper one of the magnets 12. In this orientation the lower and upper magnets 12 are magnetically attracting one-another.

An excess of the monofilament line 14 protrudes above each of the uppermost magnets 12 on opposite sides of a partial loop assembly.

Figure 3:
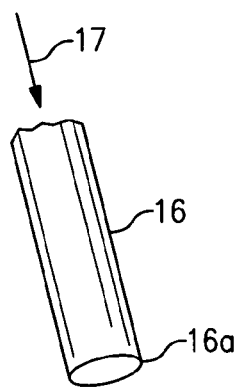
FIG. 3 is an exploded view of the magnetic tube assembly after treatment of the monofilament line and prior to placement of a cloth sleeve over the magnets.
Figure 3:
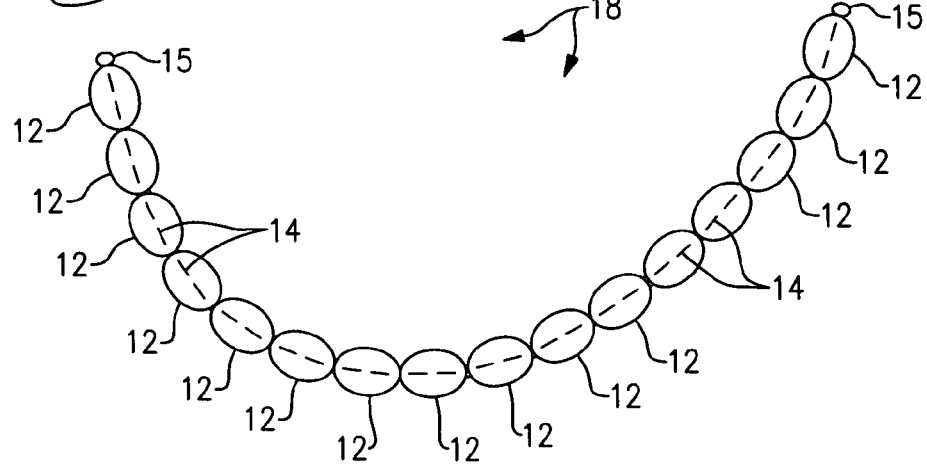

Referring now to FIG. 3, a retaining bead 15 is disposed above each of the two uppermost magnets 12. The purpose of the bead 15 is to retain the magnets 12 over the monofilament line 14 in an end to end orientation. A preferred way to create the bead 15 is to apply sufficient heat to the excess amount of the monofilament line 14 that protrudes above each of the uppermost magnets 12. The excess monofilament line 14 forms a smaller bead (not shown) that naturally descends downward to form the bead 15.

If desired, any other preferred way to form the bead 15 or otherwise retain the magnets 12 in an end to end orientation with respect to each other, can be utilized. For example, a knot (not shown) could be tied or a clip (not shown) of some type could be provided where the two beads 15 are presently located.

After the bead 15 has been included, a lower end 16a of a cloth sleeve 16 is urged in the direction of arrow 17 over the partial loop assembly that includes the magnets 12, the monofilament line 14, and the two beads 15. The cloth sleeve 16 is formed of a hollow cylindrical flexible material, such as cotton or other fabric material.

A portion of the cloth sleeve 16, as shown in FIG. 3, is disposed away from an end of the partial loop assembly. The partial loop assembly includes the magnets 12 and the monofilament line 14. The lower end 16a of the cloth sleeve 16 is fully urged over the nearest bead 15 and over the remainder of the partial loop assembly.

The longitudinal length of the cloth sleeve 16 is greater than the longitudinal length of the partial loop assembly. Therefore, after the cloth sleeve 16 has been properly disposed over the partial loop assembly, a pair of distally-opposed cloth ends 18b and 18c (See FIG. 1) extend above each of the beads 15.

After installation of the cloth sleeve 16 has been accomplished a magnetic tube assembly, as identified in general by the reference numeral 18, is provided.

Referring again primarily to FIG. 1, an elastic waist band 20 is provided. The waist band 20 includes a seam 20c where opposite ends of the waist band 20 are secured together.

A preferred method of creating the seam 20c or for attachment of the component parts to the waist band 20 or attachment of the component parts to each other includes sewing; however any preferred method of attachment is possible, such as the use of buttons, snaps, clips, VELCRO™ or the use of any other fastener (not shown).

The waist band 20 includes a front portion as identified by bracket 20a and a rear portion as identified by bracket 20b.

Each of the pair of distally-opposed cloth ends 18b and 18c of the magnetic tube assembly 18 is attached in a spaced-apart relationship with respect to each other to the front portion 20a of the waist band 20. A remainder of the magnetic tube assembly 18 forms a loop that hangs (i.e., descends) below the waist band 20.

The material used to form the waist band 20 is similar to that used to form a conventional waist band (not shown) on male underpants. This, accordingly, helps to ensure comfort for long-term wearing of the male erection enhancement loop 10. For example, well known types of elastic material in combination with a cotton fabric or other fabric material may be used to form the waist band 20 or to form other elastic component parts of the male erection enhancement loop 10, as described in greater detail below.

An elastic thigh band 22 that is formed of a similar elastic type of material as used to form the waist band 20 is attached on opposite ends 22a, 22b, thereof, and in a spaced-apart relationship to the rear portion 20b of the waist band 20. The thigh band 22 is preferably formed of a smaller size (i.e., width) material than used to form the waist band 20.

After attachment, the thigh band 22 forms a second loop that descends below the waist band 20. A center 18a of the magnetic tube assembly 18 is attached to a center of the thigh band 22. Therefore, the center 18a corresponds in location with a bottom of the loop of the magnetic tube assembly 18 and with a bottom of the second loop of the thigh band 22.

The two bottom-most magnets 12 may be urged apart with respect to each other at the center 18a of the magnetic tube assembly 18 to provide a flat portion that corresponds with the center 18a area, as shown. The flat portion allows for easier sewing (i.e., attachment). Efficacy of the male erection enhancement loop 10 is not noticeably diminished by inclusion of the flat portion at the center area 18a.

The male erection enhancement loop 10 is worn in a manner similar to a pair of underpants. The seam 20c is disposed at a rear of the wearer's trunk at approximately waist level. The male user initially urges his left foot (not shown) followed by insertion of the full length of his left leg (not shown) into the opening identified by arrow 34 simultaneous with his insertion of his right foot (not shown) followed by insertion of the full length of his right leg (not shown) into the opening identified by arrow 36. The wearer continues to urge the waist band 20 upward until the waist band 20 is disposed around the wearer's waist.

After proper placement wherein the waist band 20 encircles the waist of the wearer, a portion of the magnetic tube assembly 18 is disposed under the wearer's testicles and penis (not shown).

The male erection enhancement loop 10 is then worn for an extended period of time prior to intercourse in a manner similar to wearing underpants. After wearing of the male enhancement loop 10 for a sufficient amount of time, which can vary from person to person, the male erection enhancement loop 10 provides benefit to certain men with certain types of erectile dysfunction that helps to improve the quality and/or duration of male erection.

Optimum benefit is typically realized after the male erection enhancement loop 10 has been worn for approximately three days. It is not necessary that the male erection enhancement loop 10 be worn during actual intercourse, though for some people it may be preferable to do so. The male erection enhancement loop 10 is preferably worn both day and night to maximize its therapeutic benefit, though certain select individuals may not need to wear the male erection enhancement loop 10 while sleeping in order to obtain optimum therapeutic benefit.

The male erection enhancement loop 10 is offered in a variety of sizes to provide optimum fit, placement of the portion of the magnetic tube assembly 18 as close to the testicles and penis as possible, and prolonged comfort for long term wear. The wearer will likely have multiple identical male erection enhancement loops 10, and will change them in a manner similar to changing one's clothing for proper hygiene.

Other changes are also possible. For example, the magnets 12 can be formed of any desired material, include any preferred size and shape, and any desired magnetic strength. The magnets 12 do not have to include the openings or the monofilament line 14. For example, if desired the cloth sleeve 16 could be used to maintain the magnets 12 in the desired position to provide the necessary magnetic tube assembly 18.

The physical structure of the male erection enhancement loop 10 provides proper placement of a portion of the magnetic tube assembly 18 under the testicles and penis. This is necessary for the therapeutic benefit to occur. However, other changes in structure of the male erection enhancement loop 10 are possible providing that at least a portion of the magnetic tube assembly 18 is disposed under the wearer's testicles and penis.

The invention has been shown, described, and illustrated in substantial detail with reference to the presently preferred embodiment. It will be understood by those skilled in this art that other and further changes and modifications may be made without departing from the spirit and scope of the invention which is defined by the claims appended hereto.

What is claimed is:

1. A male erection enhancement loop for use by a male wearer who has a testicle and a penis, comprising:
   (a) a magnetic tube assembly that includes a plurality of cylindrical magnets that are generally disposed in an end to end orientation with respect to each other, wherein the magnetic tube assembly includes a longitudinal length and a pair of opposite ends;
   (b) a waist band that is able to be disposed around a waist of the wearer and wherein said pair of opposite ends of said magnetic tube assembly are attached to said waist band;
   (c) wherein when said waist band is disposed around said waist of the wearer, a portion of said magnetic tube assembly is disposed under the testicle and under the penis of the wearer;
   (d) wherein said waist band includes a seam and wherein opposite ends of said waist band are secured to each other at said seam;
   (e) wherein said pair of opposite ends of said magnetic tube assembly are attached in a spaced-apart relationship with respect to each other to a front portion of said waist band;
   (f) wherein a portion of said magnetic tube assembly is disposed below said waist band and forms a loop; and
   (g) a thigh band, wherein opposite ends of said thigh band are attached in a spaced-apart relationship with respect to each other to a rear portion of said waist band, and wherein a remainder of said thigh band is disposed below said waist band to form a second loop.

2. The male erection enhancement loop of claim 1 wherein said magnets each include an opening, there-through.

3. The male erection enhancement loop of claim 2 including a monofilament line that passes through each of said openings of said magnets and which includes means at opposite ends of said line for securing said magnets in cooperation with said line.

4. The male erection enhancement loop of claim 1 wherein said magnets include hematite magnetic rice beads.

5. The male erection enhancement loop of claim 1 wherein said magnetic tube assembly include a cloth sleeve that covers said plurality of magnets.

6. The male erection enhancement loop of claim 1 wherein a center of said magnetic tube assembly is attached to a center of said thigh band.

7. The male erection enhancement loop of claim 1 wherein said waist band is elastic.

8. The male erection enhancement loop of claim 1 wherein said thigh band is elastic.

9. A male erection enhancement loop for use by a male wearer who has a testicle and a penis, comprising:
   (a) a magnetic tube assembly that includes a plurality of cylindrical magnets that are generally disposed in an end to end orientation with respect to each other, wherein said magnetic tube assembly includes a longitudinal length and a pair of opposite ends, and wherein each of said magnets includes an opening, there-through, and a monofilament line that passes through each of said openings and which includes means at opposite ends of said line for securing said magnets in cooperation with said line, and wherein said magnets include hematite magnetic rice beads, and a cloth sleeve that covers said plurality of magnets;
   (b) a waist band that is able to be disposed around a waist of the wearer, and wherein said waist band includes a front portion and a rear portion, and wherein said waist band includes a seam, and wherein opposite ends of said waist band are secured to each other at said seam;
   (c) wherein said pair of opposite ends of said magnetic tube assembly are attached in a spaced-apart relationship with respect to each other to said front portion of said waist band, and wherein a portion of said magnetic tube assembly is disposed below said waist band and forms a loop, and a thigh band and wherein opposite ends of said thigh band are attached in a spaced-apart relationship with respect to each other to said rear portion of said waist band, and wherein a remainder of said thigh band is disposed below said waist band to form a second loop, and wherein a center of said magnetic tube assembly is attached to a center of said thigh band;
   (d) wherein said waist band is elastic and said thigh band is elastic; and
   (e) wherein when said waist band is disposed around said waist of the wearer, a portion of said magnetic tube assembly is disposed under the testicle and under the penis of the wearer.

10. The male erection enhancement loop of claim 9 wherein said cloth sleeve includes a cylindrical cloth material with a hollow center and wherein a longitudinal length of said cylindrical cloth material is greater than a combined length of said plurality of magnets and said monofilament line.

11. The male erection enhancement loop of claim 10 wherein said cloth sleeve includes cotton.

12. The male erection enhancement loop of claim 9 wherein said means at opposite ends of said line for securing said magnets in cooperation with said line includes a bead at each of said opposite ends, and wherein said bead is formed when a portion of said monofilament line that protrudes at each of said opposite ends is sufficiently heated.

\* \* \* \* \*